(12) United States Patent
Eberheim et al.

(10) Patent No.: US 8,441,267 B2
(45) Date of Patent: May 14, 2013

(54) INDUCTIVE CONDUCTIVITY-MEASURING CELL AND METHOD FOR OPERATING SUCH

(75) Inventors: Andreas Eberheim, Waldheim (DE); Thomas Nagel, Wilsdruff (DE); Marco Volker, Dobeln (DE); Hendrik Zeun, Chemnitz (DE); Andre Thieme, Geithein (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 369 days.

(21) Appl. No.: 12/801,030

(22) Filed: May 18, 2010

(65) Prior Publication Data
US 2010/0295558 A1    Nov. 25, 2010

(30) Foreign Application Priority Data
May 20, 2009    (DE) .......................... 10 2009 026 403

(51) Int. Cl.
*G01R 27/28*    (2006.01)
(52) U.S. Cl.
USPC ........................ 324/654; 324/656; 324/439

(58) Field of Classification Search ........................ None
See application file for complete search history.

(56) References Cited

U.S. PATENT DOCUMENTS

| | | | |
|---|---|---|---|
| 3,292,077 A * | 12/1966 | Sloughter | 324/445 |
| 5,341,102 A * | 8/1994 | Akiyama et al. | 324/445 |
| 5,455,513 A * | 10/1995 | Brown et al. | 324/445 |
| 5,767,682 A * | 6/1998 | Sekimoto et al. | 324/445 |
| 5,793,214 A * | 8/1998 | Wakamatsu | 324/601 |
| 6,414,493 B1 | 7/2002 | Rezvani | |
| 6,812,709 B2 * | 11/2004 | Wieland et al. | 324/445 |

FOREIGN PATENT DOCUMENTS

| | | |
|---|---|---|
| DE | 41 16 468 A2 | 11/1992 |
| DE | 198 51 146 A1 | 5/2000 |
| DE | 100 45 583 A1 | 3/2002 |

* cited by examiner

*Primary Examiner* — Minh N Tang
(74) *Attorney, Agent, or Firm* — Bacon & Thomas, PLLC

(57) ABSTRACT

A method for operating an inductive conductivity-measuring cell having a primary circuit with a sending coil, a secondary circuit with a receiver coil, and a short-circuit path, which passes through the sending coil and the receiver coil. The sending coil couples via the short-circuit path inductively with the receiver coil, wherein, in the case of closed short-circuit path, a first electrical signal present in the primary circuit is measured, and wherein the first signal is compared with, and/or weighed against, values, which are furnished or stored.

13 Claims, 2 Drawing Sheets

INDUCTIVE CONDUCTIVITY-MEASURING CELL AND METHOD FOR OPERATING SUCH

TECHNICAL FIELD

The invention relates to a method for operating an inductive conductivity-measuring cell having a primary circuit with a sending coil and a secondary circuit with a receiver coil, as well as having a short-circuit path, which passes through the sending coil and the receiver coil, wherein the sending coil couples inductively with the receiver coil via the short-circuit path.

Additionally, the invention relates to an inductive conductivity-measuring cell having a primary circuit, which contains a sending coil, and a secondary circuit containing a receiver coil, as well as having a short-circuit path, which passes through the sending coil and the receiver coil.

BACKGROUND DISCUSSION

Such measuring cells have, for example, a sending coil embodied as a toroidal coil, which is fed by an alternating voltage. In the interior of the sending coil, an annular, magnetic, alternating field is produced. In the same plane in which also the sending coil lies, a receiver coil is arranged, which likewise can be embodied as a toroidal coil. Through movable ions in the liquid, measured material, as a result of the magnetic alternating field in the sending coil, a ring shaped electrical current is produced in the measured material, which, in turn, causes in the receiver coil an output signal, whose strength is dependent on the mobility and concentration of the ions and, consequently, on the electrical conductivity of the liquid, measured material. The output signal is usually in the form of an induced current.

The principle is, per se, established in industrial process measurements technology and discussed in a number of documents of the patents literature, examples of which include U.S. Pat. No. 3,603,873 and German Offenlegungsschrift (Laid-Open Application) DE 198 51 146 A1.

For Ex-protection reasons, a resistor $R_A$ can be inserted in the secondary circuit. If the output signal is tapped as voltage $U_{Ind}$ from the receiver coil, the following relationship holds:

$$U_{Ind} = R_A \cdot I_{Ind} = \frac{N_1}{N_2} \frac{1}{1 + N_2 \cdot R_{Med} \cdot \left(\frac{1}{R_A} + \frac{1}{j\omega L_2}\right)} U_{Ex},$$

where $N_1$ is the number of turns of the sending coil and $N_2$ the number of turns of the receiver coil. $R_{Med}$ refers to the resistance of the measured material, j is the imaginary unit and $\omega$ the angular frequency of $2\pi f$, wherein f is the frequency of the induced alternating current. Furthermore, $U_{Ex}$ refers to the exciter voltage and $I_{Ind}$ the electrical current induced in the receiver coil of inductance $L_2$.

In case $R_A \ll \omega L_2$, then the inductance $L_2$ of the secondary coil has a negligible influence on the measured value.

If $R_A \lesssim \omega L_2$ is no longer true, then the measured value becomes dependent on the inductance $L_2$ of the receiver coil. This inductance $L_2$, in turn, depends on the core permeability, which is a function of temperature. Therewith, the measured value is temperature dependent (order of magnitude: About 1% per 100° C.). In order to compensate for this, it is important to determine the inductance of the receiver coil. For example, especially in the case of sterilization procedures, where the conductivity-measuring cell experiences, up to 30 times daily, temperature fluctuations between 5° and 150° C., a diagnosis of the sending- and/or receiver coil and an associated adjusting of the measured value is required in accordance therewith.

From U.S. Pat. No. 6,414,493 B1 and German Offenlegungsschrift (Laid-Open Application) DE 4116468 A1, as well as also from German Patent DE 1028679, it is known to provide an additional conductor loop, which passes through the sending coil and through the receiver coil and serves as an additional, short-circuit path. For diagnostic purposes, the conductor loop is closed and an electrical signal induced in the receiver coil, or in the secondary circuit, and ascertained by means of an evaluation unit connected to the receiver coil, or to the secondary circuit. From the induced output signal, a state of the receiver coil, especially damage to such, can be ascertained.

Moreover, it is known from European Offenlegungsschrift (Laid-Open Application) EP 0999441 A1, for monitoring the sending coil of inductive conductivity-measuring cells, to determine the inductance by means of electrical current, or voltage, measurement. The receiver coil of the secondary circuit can, however, not be reliably monitored therewith.

SUMMARY OF THE INVENTION

An object of the invention, therefore, is to provide an inductive conductivity-measuring cell and a method for operating such, in the case of which a state of the measuring cell, especially damage to the sending coil, above all, however, to the receiver coil, can be ascertained.

The object is achieved, as regards the method of the invention, by features including that, in the case of closed short-circuit path, a first electrical signal present in the primary circuit is measured, and that the first signal is compared with, and/or weighed against, values, which are furnished or stored.

In such case, the invention makes use of the fact that the sending coil in the case of a closed short-circuit path inductively couples with the receiver coil. In the case of a closed short-circuit path, the sending coil and the receiver coil can, for example, be represented in an equivalent circuit diagram of the primary circuit as one coil. Alternatively, in the equivalent circuit diagram, the sending coil can be represented as parallel to the receiver coil. The closed short-circuit path forms, in such case, a defined inductive coupling between the sending and the receiver coils, so that, on the basis of a deviation from a value ascertained e.g. by calibrating, a state of the receiver, and/or of the sending, coil can be detected. The secondary circuit needs no specialized, extra evaluation unit for registering a defect or for determining a state of the measuring cell, especially of the receiver coil. According to the invention, thus, sufficient for diagnostic purposes is the measuring of a first electrical signal in the primary circuit in the case of closed short-circuit path, via which a defined inductive coupling occurs between the sending and receiver coils.

In an embodiment of the method, in the case of interrupted short-circuit path, a second electrical signal present in the primary circuit is measured, and the first signal and the second signal are compared with, and/or weighed against, one another and/or furnished, or stored, values. If the short-circuit path is open, then the coils are decoupled from one another and in the primary circuit then only the sending coil is still present, or "visible". In this way, a physical variable representing a state of the sending coil can be determined. From the first and second signals tapped from the primary circuit, then a state of the receiver coil can be deduced. For determining the state of the receiver coil, it is thus only necessary to provide means in the primary circuit for measuring the first and second electrical signals. The first and/or second electrical signals can be, for example, the short-circuit current of the sending and/or receiver coil or a variable derived therefrom.

In an embodiment of the method, the inductance and/or the impedance or a therefrom derived variable of the receiver coil is ascertained by means of the first and the second electrical signals. Through the adaptive determining (i.e. a determining matched to the respective measuring conditions, or environmental conditions, as, for example, the ambient temperature), for example, of the inductance of the receiver coil, the influence of the receiver coil on the measurement signal, and, therewith, on the actual measured value, can be lessened. The method of the invention improves, thus, the measured value accuracy, for example, as a function of the temperature. Additionally, the measuring can occur via a defined impedance in the secondary circuit. In this way, a defect, such as, for example, a wire break between the receiver coil and a measuring, or evaluating, circuit can be detected. Moreover, the inductance of the sending, and/or receiver, coil can be registered for purposes of preventive, or predictive, maintenance of the measuring cell.

In an additional embodiment of the method, the inductance and/or the impedance of the sending coil is ascertained by means of the second signal. In the case of interrupted short-circuit path, as already mentioned, the second electrical signal tapped in the primary circuit is, above all, dependent on the inductance of the sending coil. By means of the first electrical signal, which is measured in the case of closed short-circuit path, the inductance and/or the impedance, especially the resistance, also of the receiver coil can be ascertained, or deduced, therefrom, since the first electrical signal in the primary circuit, which is measured in the case of closed short-circuit path, also is dependent on the inductance of the receiver coil.

In an additional embodiment of the method, the first and the second electrical signal are measured by means connected electrically only with the primary circuit. For such purpose, for example, an evaluation unit can be connected to the primary circuit or in the sending coil for determining electrical current and electrical voltage.

In an additional embodiment of the method, a first short-circuit path is formed by the measured material. In an additional embodiment of the method, a second short-circuit path is formed with a conductor loop. The short-circuit path can thus be realized by the measured material and/or by means of a conductor loop passing through the sending and receiver coils. If the short-circuit path is formed, for example, only by the measured material, the conductivity-measuring cell can, for example, be removed from the measured material, in order to interrupt, or terminate, the short-circuit path, so that the measured material no longer passes through the sending coil and the receiver coil.

In an additional embodiment of the method, a switch element is provided, via which the short-circuit path, especially a short-circuit path based on a conductor loop, is opened, or closed, such that, thereby, the sending coil is decoupled, or coupled, as the case may be, with the receiver coil via the short-circuit path.

In an additional embodiment of the method, the first electrical signal is measured in the case of opened secondary circuit. In an additional embodiment of the method, the first electrical signal is measured in the case of closed secondary circuit. In an additional embodiment of the method, the first electrical signal is measured in the case of secondary circuit terminated via a resistor R. In the case of closed secondary circuit, the terminating impedance of the receiver coil can be measured. Thus, for example, a wire break between receiver coil and an evaluation unit can be determined, since, in the case of a wire break, the terminating impedance can no longer be measured. A very large terminating impedance corresponds quasi to an open secondary circuit.

In an additional embodiment of the method, by means of the sending coil, an alternating voltage signal is transmitted to the secondary circuit, and essentially the receiver coil is used for receiving the alternating voltage signal.

In an additional embodiment of the method, the receiver coil, especially during a measuring for determining conductivity of the measured material or during a calibration procedure, is coupled to the sending coil by closing the short-circuit path.

As regards the inductive conductivity-measuring cell, the object of the invention is achieved by features that a first evaluation unit is connected to the primary circuit for measuring an electrical signal, and that the evaluation unit serves for evaluating a first electrical signal recorded in the case of closed short-circuit path.

In an embodiment of the inductive conductivity-measuring cell, a switching unit is provided for opening, or closing, the short-circuit path, and the evaluation unit serves to compare with the first signal, and/or to weigh against the first signal, a second electrical signal measured in the case of interrupted short-circuit path.

In an embodiment of the inductive conductivity-measuring cell, another switching unit is provided in the secondary circuit, which short-circuits the secondary winding, especially via a resistor, interrupts the secondary circuit or connects with an evaluation unit for determining the electrical conductivity of the measured material.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
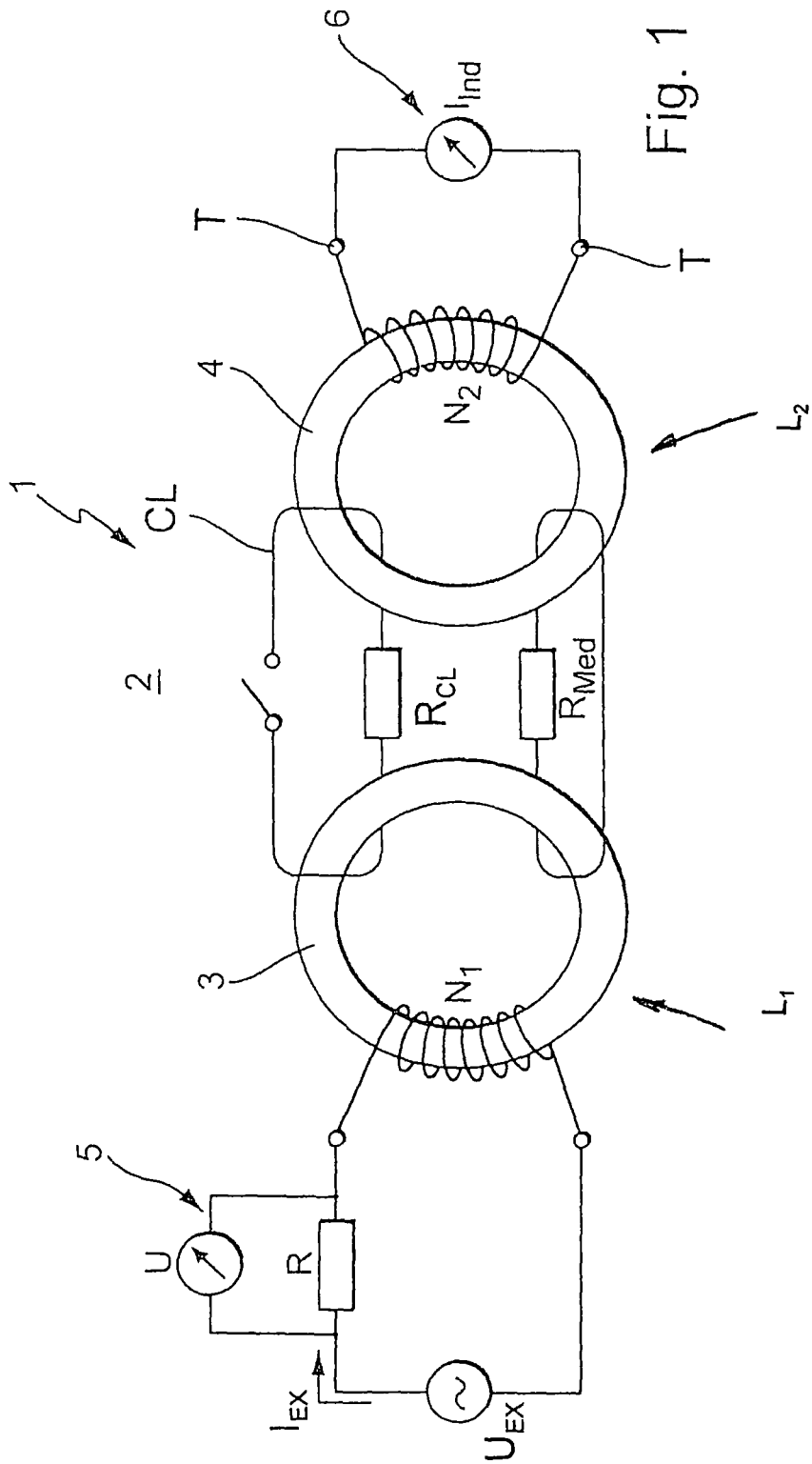
FIG. 1 is a schematic representation of an inductive conductivity-measuring cell.

FIG. 1 shows a schematic representation of an inductive conductivity-measuring cell 1. The measuring cell 1 serve for measuring the electrical conductivity of a liquid, measured material 2. The coils $L_1$, $L_2$ include, supplementally, coil cores 3, 4. A measuring of the inductance of the sending coil $L_1$ and the receiver coil $L_2$ can be used to monitor the functioning of the measuring cell 1. Defects, such as contact interruption or coil-coil faults, can, in this way, be recognized. According to the invention, measuring of the inductance of the sending and receiver coils $L_1$, $L_2$ is provided in the installed state, i.e. during the process. The measuring occurs in two steps:
1) Measuring the inductance of the sending coil $L_1$ via electrical current, and voltage, measurement in the primary circuit.
2) By coupling the receiver coil $L_2$ by means of a short-circuit path, especially a 0Ω short-circuit conductor loop, the two coils $L_1$, $L_2$ are connected in parallel.

Through renewed measuring on the primary side, one obtains the inductance of both parallelly connected coils. From both values, then the inductance of the receiver coil $L_2$ can be calculated.

The terminals T of the receiver coil can also be "open" (not shown).

The method permits the lessening of the influence of the inductance of the receiver coil $L_2$ on the actual measured value. The measuring can occur by means of an installed $0\Omega$ conductor loop (which can, for example, be switchable via a relay in the measuring cell, this not being shown) during measuring or during a calibration procedure. In this way, the measured values can be adjusted on the basis of current inductance values $L_1$, $L_2$.

Figure 2:
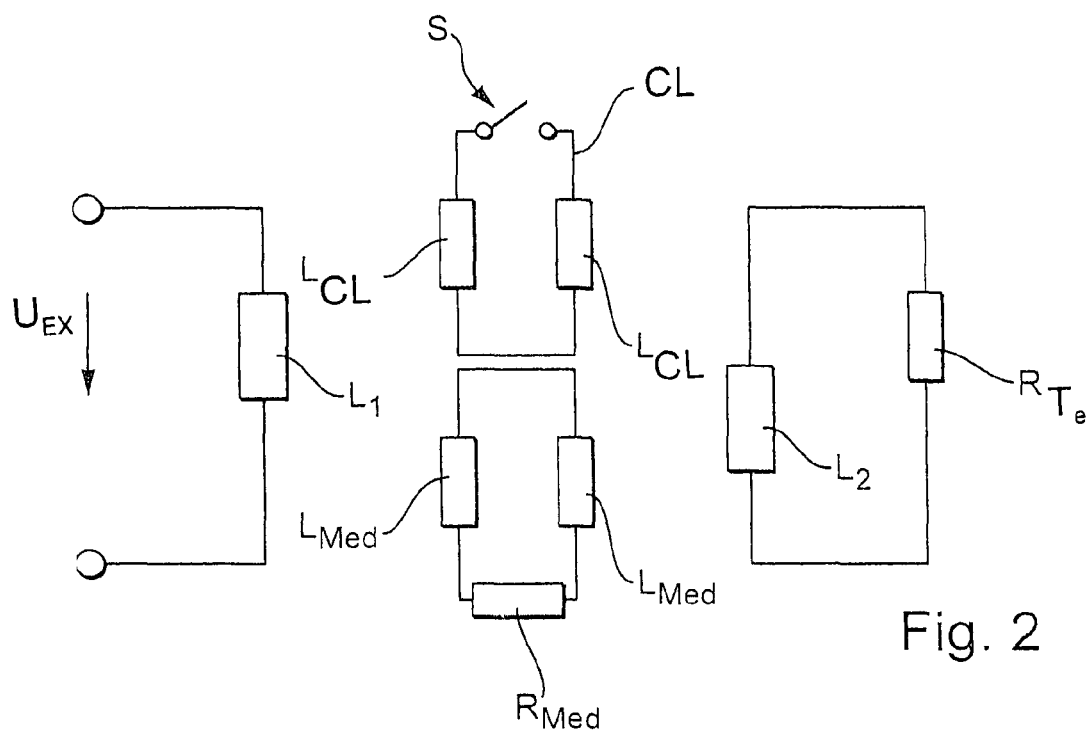
FIG. 2 is a detailed equivalent circuit diagram of an inductive conductivity-measuring cell.
Figure 3:
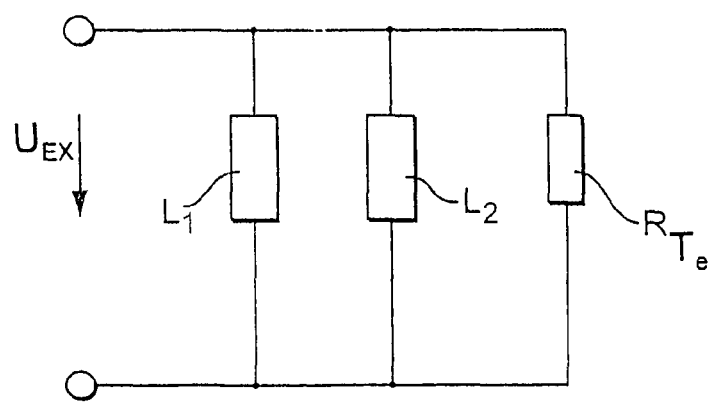
FIG. 3 is a simplified equivalent circuit diagram of the inductive conductivity-measuring cell of FIG. 2.

Additionally, the receiver coil can be terminated via a defined impedance (see FIGS. 2 and 3). In this case, the terminating impedance of the receiver coil is measurable in the case of closed short-circuit path also on the primary side. In this way, a wire break between receiver coil $L_2$ and measurement circuit 6 can be detected, since, in the case of a wire break, the terminating impedance $R_{Te}$ can no longer be measured.

By suitable evaluation of the first and/or second signal in the case of measuring with opened receiver coil $L_2$, besides coil inductance, also the series, or parallel, equivalent resistances of the coils can be ascertained. These are dependent, among other things, on parasitic effects (for example, aging of, or damage to, the cores 3, 4) of the core material, so that, also as regards this aspect, diagnostic measures and a correction of the measured value are available.

The measuring of inductance of the sending, and/or the receiving, coil $L_1$, $L_2$ can occur, for example, in each measuring of the electrical conductivity of the measured material 2. On the other hand, a measuring of the inductance of the sending, and/or of the receiving, coil $L_1$, $L_2$ at fixedly predetermined time intervals is another option. Furthermore, the measuring of the inductance of the sending, and/or the receiving, coil $L_1$, $L_2$ can occur in temperature, and/or measuring range, dependent intervals. For such purpose, criteria for the monitoring can be stored in the measuring cell.

By means of a second switching unit (not shown) arranged in the secondary circuit, it is possible to switch between different operating modes:

1) In a first operating mode, in the case of interrupted short-circuit path, i.e. in the case of opened conductor loop CL, the electrical conductivity of the measured material 2 can be ascertained. Additionally, by means arranged on the primary side, the inductance of the sending coil $L_1$ can be ascertained. Via magnitude and phase of the voltage in the primary circuit, then the impedance of the sending coil $L_1$ can be calculated.

2) In a second, measurement operation, the inductance of the receiver coil $L_2$ can be ascertained. For such purpose, the switch S and, therewith, the conductor loop, i.e. the short-circuit path, is closed. Again, via magnitude and phase of the voltage in the primary circuit, this time in the case of closed short-circuit path, the impedance in the primary circuit can be ascertained. In the case of, for example, impedance of the sending coil $L_1$ known from the first operating mode, the impedance of the receiver coil $L_2$ can then be calculated.

3) In a third operating mode, in the case of closed short-circuit path and in the case of a receiver coil $L_2$ terminated via a resistor, a wire break can be detected. The resistor $R_{Te}$ must, for this, be measurable in parallel with the impedances of the sending coil $L_1$ and the receiver coil $L_2$.

The sending coil $L_1$ includes a turns $N_1$ and an evaluation unit 5. Flowing to the evaluation unit 5 is current $I_{EX}$, while the receiving coil $I_2$ includes turns $N_2$ and an additional evaluation unit 6. A conductor loop $C_L$ is situated between the cores 3 and 4. This loop includes a resistor $R_{CL}$. The receiver coil $L_2$ includes terminals T which connects the turns $N_2$ to the additional unit 6.

FIG. 2 shows an equivalent circuit diagram of an inductive conductivity-measuring cell 1. Applied to the primary circuit is an alternating voltage $U_{Ex}$. The alternating circuit includes a sending coil with an inductance $L_1$. The secondary circuit is composed of a receiver coil with inductance $L_2$. The sending and receiver coils $L_1$, $L_2$ can inductively couple with one another via a conductor loop CL, or the measured material 2. The inductance of the measured material 2 is, in such case, equivalently represented by $L_{Med}$. Additionally, the measured material 2 has a resistance $R_{Med}$, while the conductor loop CL has, for example, as shown in FIG. 2, an idealized resistance of 0 ohm. The conductor loop CL can be closed or opened via a switch S.

The secondary circuit is terminated via a termination resistor $R_{Te}$.

If switch S is closed, then the coupling via the conductor loop CL dominates and the inductive coupling via the measured material 2 is negligibly small. The arrangement shown in FIG. 2 is then analogous to a loaded, double transformer.

The equivalent circuit diagram can be simplified to the circuit diagram illustrated in FIG. 3. The sending coil with inductance $L_1$, the receiver coil with inductance $L_2$ and the termination resistor $R_{Te}$ are connected in parallel with one another. By means of the measured first and second electrical signals, thus the inductance of the receiver coil $L_2$ can be ascertained.

The conductor loop CL includes inductance $L_{CL}$, and the inductance of the measured material is represented by $L_{Med}$.

The invention claimed is:

1. A method for operating an inductive conductivity-measuring cell having a primary circuit with a sending coil, a secondary circuit with a receiver coil, and a short-circuit path, which passes through the sending coil and the receiver coil, comprising the steps of:

coupling the sending coil via the short-circuit path inductively with the receiver coil;

measuring, in the case of a closed short-circuit path, a first electrical signal present in the primary circuit;

comparing the first electrical signal with, and/or weighed against, values, which are furnished or stored;

measuring, in the case of an interrupted short-circuit path, a second electrical signal present in the primary circuit;

comparing the first electrical signal and the second electrical signal with, and/or weighed against, one another and/or furnished, or stored, values; and whereas the first and second electrical signals are measured by means of an electrical connection only with the primary circuit.

2. The method as claimed in claim 1, further comprising the step of:

ascertaining inductance and/or impedance, or a variable derived therefrom, for the receiver coil by means of the first and/or the second electrical signal.

3. The method as claimed in claim 1, further comprising the step of:

ascertaining inductance and/or impedance, or a variable derived therefrom, for the sending coil by means of the first and/or second signal.

4. The method as claimed in claim 1, further comprising the step of:

performing a first short-circuit path by a measured material.

5. The method as claimed in claim 1, further comprising the step of:
performing a second short-circuit path by a conductor loop.

6. The method as claimed in claim 1, further comprising the step of:
providing a switch element, via which the short-circuit path is opened, or closed, and, thereby, the sending coil is decoupled from, or coupled with, the receiver coil via the short-circuit path.

7. The method as claimed in claim 1, further comprising the step of:
measuring the first signal in the case of an opened secondary circuit.

8. The method as claimed in claim 1, further comprising the step of:
measuring the first signal in the case of a closed secondary circuit.

9. The method as claimed in claim 1, further comprising the step of:
measuring the first signal in the case of a secondary circuit terminated via a resistor.

10. The method as claimed in claim 1, further comprising the step of:
transmitting an alternating voltage signal to the secondary circuit by means of the sending coil; and
essentially the receiver coil is used for receiving the alternating voltage signal.

11. The method as claimed in claim 1, further comprising the step of:
coupling the receiver coil to the sending coil by closing the short-circuit path, especially during a measurement for determining conductivity of the measured material or during a calibration procedure.

12. An inductive conductivity-measuring cell comprising:
a primary circuit, which contains a sending coil, and a secondary circuit containing a receiver coil;
a short-circuit path, which passes through the sending coil and the receiver coil;
an evaluation unit connected to said primary circuit for measuring an electrical signal, said evaluation unit serves for evaluating a first electrical signal recorded in the case of a closed short-circuit path; and
a switch element for opening or closing the short-circuit path, wherein:
said evaluation unit serves for comparing with the first electrical signal, and/or weighing against the first electrical signal, a second electrical signal measured in the case of interrupted short-circuit path.

13. The inductive conductivity-measuring cell as claimed in claim 12, further comprising:
an additional evaluation unit; and
a further switch element in the secondary circuit, which serves to short-circuit said secondary coil, especially via a resistor, to interrupt said secondary circuit and/or to connect with said additional evaluation unit for determining electrical conductivity of a measured material.

* * * * *